United States Patent [19]

Gaunaurd et al.

[11] 4,249,422
[45] Feb. 10, 1981

[54] APPARATUS AND PROCESS FOR DETERMINING THE COMPOSITION OF FLUID-FILLED CAVITIES

[75] Inventors: Guillermo C. Gaunaurd, Rockville; Herbert M. Überall, Bethesda, both of Md.

[73] Assignee: The United States of America as represented by the Secretary of the Navy, Washington, D.C.

[21] Appl. No.: 87,270

[22] Filed: Oct. 22, 1979

[51] Int. Cl.³ ............................................. G01N 29/00
[52] U.S. Cl. ........................................ 73/589; 73/602; 73/659
[58] Field of Search ................. 73/579, 589, 596, 597, 73/599, 602, 658, 659; 367/38, 40, 47, 48, 49

[56] References Cited

U.S. PATENT DOCUMENTS

| 3,710,615 | 1/1973 | Johnson et al. | 73/589 |
| 3,791,200 | 2/1974 | Hayre | 73/589 |
| 3,914,984 | 10/1975 | Wade | 73/599 |
| 3,946,600 | 3/1976 | Rettig et al. | 73/658 |
| 4,006,625 | 2/1977 | Davis | 73/659 |
| 4,086,816 | 5/1978 | Jon et al. | 73/587 |
| 4,086,817 | 5/1978 | Jon et al. | 73/587 |
| 4,117,732 | 10/1978 | Brazhnikov | 73/599 |
| 4,140,021 | 2/1979 | Nomura et al. | 73/587 |
| 4,144,766 | 3/1979 | Wehrmeister | 73/587 |

OTHER PUBLICATIONS

E. Meyer et al., "Pulsation Oscillations of Cavities in Rubber," *J. Acoust. Soc. Am.*, vol. 30, No. 12, pp. 1116–1124, Dec. 1958.

G. Gaunaurd et al., "New Method to Determine Shear Absorption using Viscoelastodynamic Resonance-Scattering Formalism," *J. Acoust. Soc. Am.*, vol. 64, No. 4, pp. 1211–1212, Oct. 1978.

G. Gaunaurd et al., "Deciphering Scattering Code Contained in Resonance Echoes from Fluid Filled Cavities in Solids," *Science*, vol. 206, pp. 61–64, Oct. 1979.

*Primary Examiner*—Stephen A. Kreitman
*Attorney, Agent, or Firm*—R. S. Sciascia; A. L. Branning; D. A. Lashmit

[57] ABSTRACT

An apparatus and method for determining the material properties characterizing a fluid contained in a cavity inside a solid comprises analyzing the resonances in the amplitude of elastic waves scattered by the cavity. Specifically, the resonance positions and their widths are used to determine the sound speed and the density of the cavity filler. The sound speed is found from the spacing between two consecutive overtones of any mode, which asymptotically becomes uniform for the higher-index overtones. The density is obtained from the width of any high order resonance and accordingly, all the information about the material composition of the filler is contained, and can be extracted, from the high-frequency asymptotic region.

7 Claims, 8 Drawing Figures

APPARATUS AND PROCESS FOR DETERMINING THE COMPOSITION OF FLUID-FILLED CAVITIES

BACKGROUND OF THE INVENTION

The present invention relates to diciphering elastic wave scattering by obstacles in continuous media, and more particularly pertains to a new and improved apparatus and method for deciphering the resonant echoes from fluid-filled cavities in solids so as to identify the material composition of the filler fluid.

In the fields of material science and physics, it is often important and desirable to identify the composition of inclusions contained within various materials. For example, in medical ultrasonics it is important to determine the material composition of some fluid-like substances, e.g., tumors, contained in animal tissue by ultrasonically scanning these "in vivo" with monitored sound projectors. In the area of non-destructive testing and materials evaluation, a basic problem of daily routine occurrence is to determine if a material obstacle is contained within another "host" material, and if so, what kind of obstacle it is. Explosive grains, bombs, etc., are routinely tested non-destructively (acoustically or with x-rays) to determine the presence of material imperfections, flaws, or inhomogeneities in them. In geophysics, seismic waves scattered by fluid-filled caverns in the earth's crust, carry information about the material composition of the cavern's contents. The Army has used these to determine the presence of silo-sites in foreign countries.

The search for a satisfactory method of both locating a cavity and non-destructively determining the composition of the same has recently intensified due to world-wide energy shortages. Obviously, a perfected process might be utilized to locate and identify oil, water and gas deposits contained in cavities within the earth's interior.

Acoustical analysis has long been recognized as one of the more desirable techniques of locating obstacles contained within solid materials. There have been numerous methods developed for analyzing the elastic wave scattering caused by obstacles in nonabsorbing media. A good part of the prior art methods have utilized spherical geometry, and most of the incident wave-types considered have been continuous wave signals, although some transient result methods are available for continuous wave excitations. The cases of pure plane p-wave incidence or pure s-wave incidence have been studied in some detail. The obstacle has been taken to be an elastic sphere of properties different from those of the medium into which it is embedded, a rigid inclusion, a fluid-filled cavity, an evacuated cavity, or more general situations. Other more general cavity shapes from spheriodal or ellipsoidal, to completely arbitrary have also been analyzed, and general matrix theories for elastic wave-scattering situations have recently been developed.

Some of the prior art has analyzed the stress and displacement fields, or the stress concentrations which dynamically develop in the elastic material as a result of the wave scattering by the cavity, while other prior art has discussed the backscattering cross-sectional amplitudes of p or s waves incident upon the cavity. With few exceptions, the numerical calculations are sparse, pertain only to a few metals, and are mostly restricted to the low frequency, i.e., Rayleigh, regime. Although some of the prior art has attributed the rapid oscillations in cross-sectional values to some sort of resonant phenomena, no attempt has been made to actually cast the analysis in some explicit resonant form. In effect, the amplitudes of backscattered waves returned by fluid-filled cavities in viscoelastic solids, when plotted as a function of frequency, exhibit so many rapid oscillations and complicated features that until very recently it did not appear possible to extract the physical information contained in them.

SUMMARY OF THE INVENTION

The general purpose of the invention is to provide a new process whereby the amplitudes of backscattered waves can be analyzed and thus be used to identify, for a given shape of a cavity, the material composition of the filler substance.

An object of the present invention is the provision of an apparatus and process for analyzing fluid-filled cavities in a solid.

Another object is to provide a means for identifying the material composition of a filler fluid contained within a body.

A further object of the invention is the provision of a process and apparatus for studying the scattering of a plane p-wave by a fluid-filled spherical cavity in elastic and viscoelastic media.

BRIEF DESCRIPTION OF THE DRAWINGS

Other objects and many of the attendant advantages of this invention will be readily appreciated as the same becomes better understood by reference to the following detailed description when considered in connection with the accompanying drawings, in which like reference numerals designate like parts throughout the figures thereof and wherein.

DESCRIPTION OF THE PREFERRED EMBODIMENT

Figure 1:
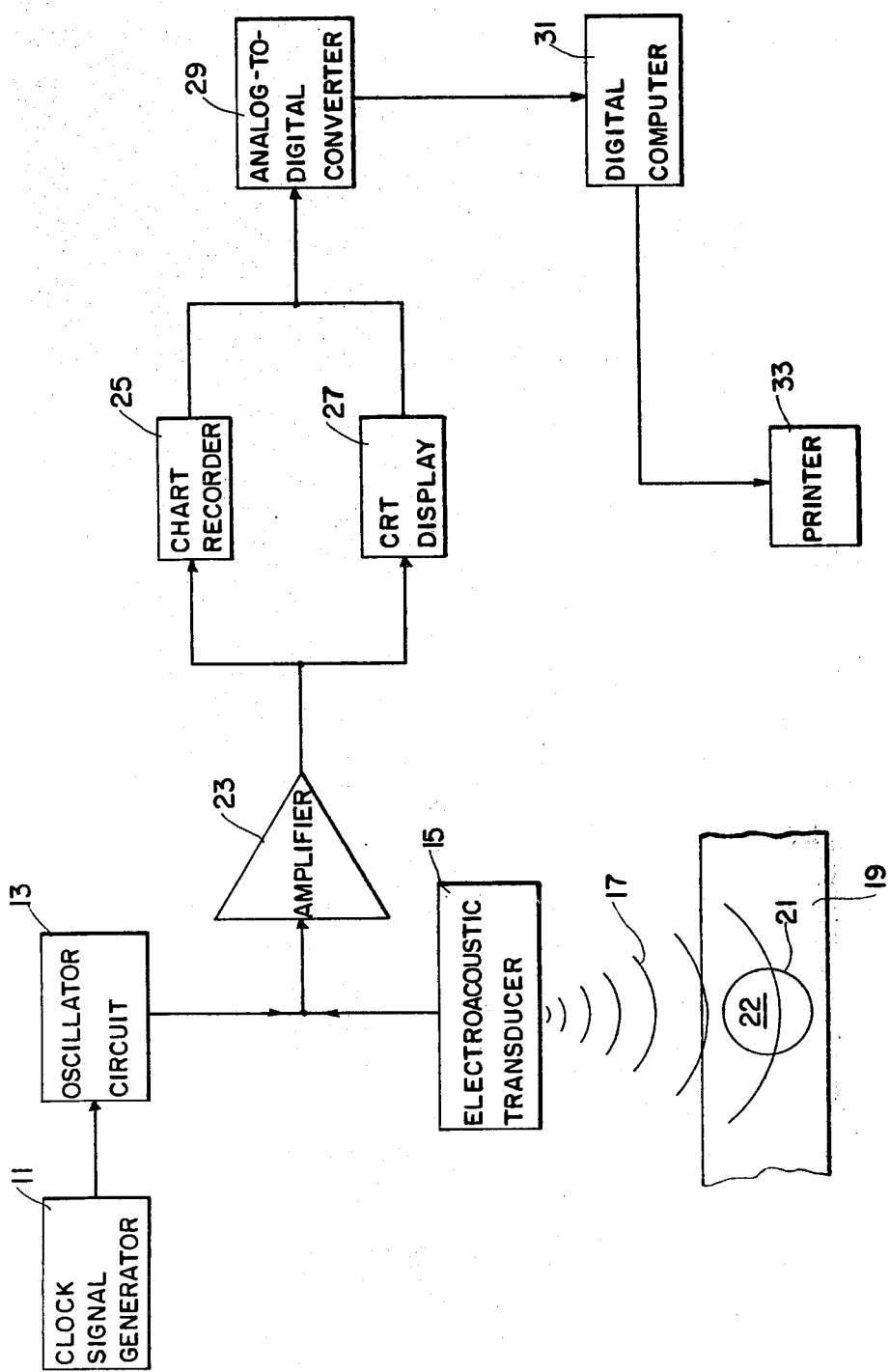
FIG. 1 shows a schematic of a preferred embodiment of the apparatus utilized to perform the process of the present invention.

FIG. 1, which illustrates one embodiment of an apparatus which might be utilized to perform the process of the present invention, shows a clock signal generator 11 which drives an oscillator circuit 13. The oscillator circuit 13 delivers pulses which excite an electroacoustic transducer 15 so that the latter generates acoustic pulses 17 of a known frequency spectrum. An elastic or viscoelastic material 19 having an internal cavity 21 filled with a fluid 22 is situated so that the pulses 17 may propagate therethrough. The transducer 15, acting in its receiving mode, receives the echoes of the backscattered acoustic pulses which reflect from the cavity 21, and an amplifier 23 supplies these pulse signals to a chart recorder 25 or a cathode ray tube (CRT) display 27. The signals may then be analyzed manually or may be applied to an analog-to-digital converter 29 and then deciphered by a digital computer 31 containing a program written to perform the manual analysis. The process step involving the manual analysis will be explained later.

The output of the digital computer 31 may be then provided by a printer 33.

In operation, the clock signal generator 11 provides a continuous series of timing pulses to the pulse generator or oscillator circuit 13. The pulse generator generates alternating-current power at a frequency determined by the values of certain constants in its circuits. In effect, the pulse generator serves as an amplifier having a positive feedback and having circuit parameters that restrict the oscillations of the device to a single known frequency.

The oscillations from the pulse generator 13 excite the electroacoustic transducer 15 to change the electrical energy received from the generator into acoustic energy or pulses 17.

The compressional sound waves 17 propagate through the elastic or viscoelastic material 19 and upon striking the cavity 21 having the fluid 22 contained therein, a portion of the waves are scattered. The backscattered "echo" is monostatically picked-up by the transducer that sent the ping, and is now operating in the receiving mode. The received signals are then supplied to the amplifier 23 for amplification.

The amplified signals may then be recorded on a chart by means of chart recorder 25, or they might be displayed on the CRT display 27 and then photographed. In either case, a graph of the signal waveforms is obtained and the analysis as described below may be accomplished.

The analysis is based upon the fact that when the spherical filler 22 is set into oscillation by elastic, e.g., compressional, waves incident upon it, a set of modal resonances (fundamental and overtones) are created. These resonances characterize the filler 22 as if they were its signature. Since incident shear waves excite the same resonances in the filler 22, the analysis may be limited to incident compressional waves. From the usual spectral plots of the backscattered wave amplitudes versus non-dimensional frequency $x \equiv k_d a$, it is possible to obtain these resonances which manifest themselves as narrow lines or wide "spikes". (NOTE: $k_d = \omega/c_d$, $\omega$ = circular frequency of the incident wave, $c_d$ = speed of compressional waves, a = radius of the cavity.) These plots display a quantity which, for simplicity, will henceforth be called "the echo". The way the resonances of an unknown filler are thus being used for material discrimination purposes resembles the way chemical elements are identified from their optical spectra.

The plane p (i.e., compressional) elastic waves incident on fluid-filled spherical cavities in solids produce two scattered waves, one compressional and the other of shear or s type. The scattering amplitudes $f^{pp}$ or $f^{ps}$ of both of these scattered waves could be analyzed, but the instant process may be completed by analyzing either.

Analyzing $f^{pp}(\theta)$, the non-mode converted, normalized amplitude can be shown to be $$f^{pp}(\theta)/a = \sum_{n=0}^{\infty} f_n^{pp}(\theta)/a = \sum_{n=0}^{\infty} \frac{(2n+1)}{ik_d a} A_n P_n(\cos\theta) \quad (1)$$

where $A_n$ are coefficients given by ratios of two $3 \times 3$ determinants whose elements contain products of the filler-to-matrix density ratio (i.e., $\rho_f/\rho$) with various spherical Bessel and Hankel functions and their derivatives, of arguments $k_d a$ and $k_s a$, and of order n. These elements of course are determined from the boundary condition of the problem.

Figure 2:
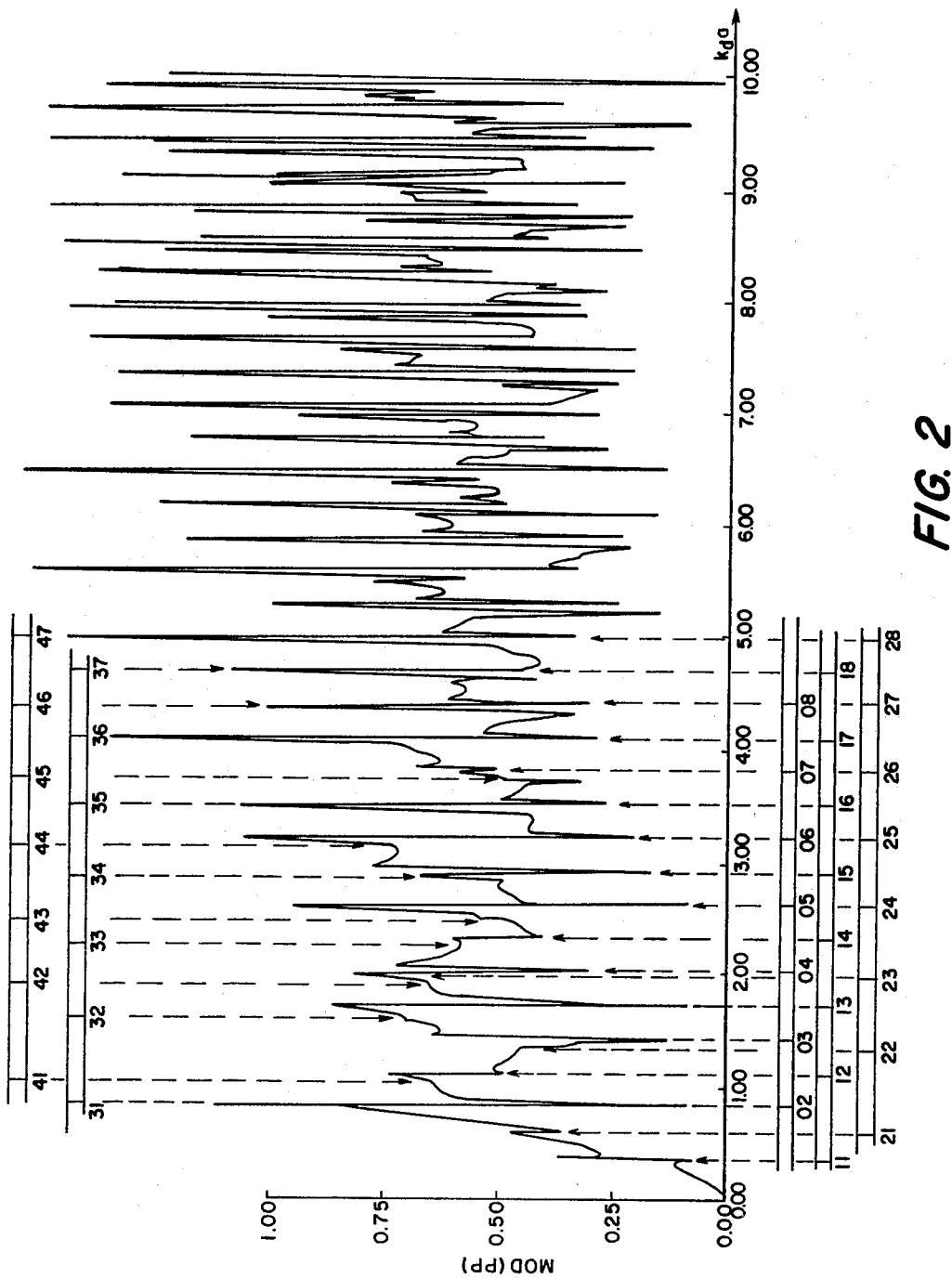
FIG. 2 is a graph illustrating the modulus of the summed backscattering amplitude for an alcohol-filled spherical cavity in an aluminum matrix.

In the backscattering direction $\theta = \pi$, the Legendre polynominals are simplified by means of the relation $P_n (\cos \pi) = (-1)^n$. FIG. 2 shows the plot of the modulus of this summed backscattered amplitude for a cavity filled with ethyl alcohol in an aluminum matrix. This is the "echo" containing the rapid oscillations and complex features mentioned above. Adding fifteen partial waves (n=0,1 ... 14) in the sum of Eq. (1) with $\theta = \pi$, suffices to produce an accurate graph in the range $0 \leq x \equiv k_d a \leq 10$ of FIG. 2. Considerable simplification is introduced by the analysis of each individual partial-wave contribution rather than of the summed echo amplitude.

Figure 3:
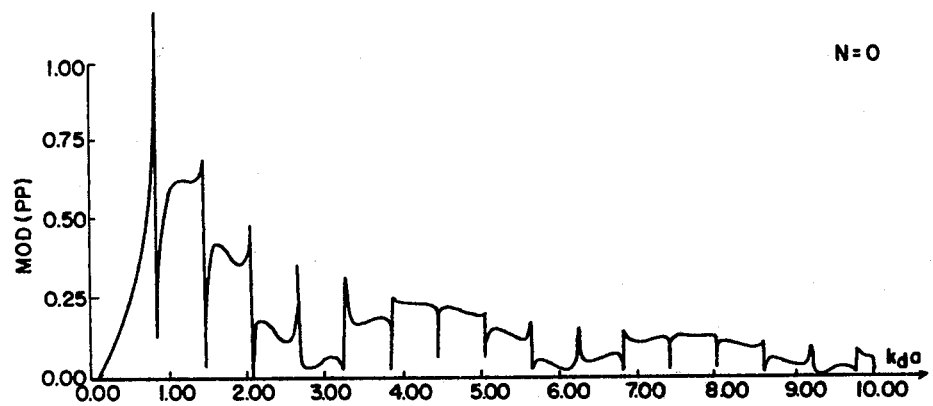
FIGS. 3-4 are graphs showing the alcohol in aluminum amplitude moduli of the first two modes (n=0, 1) respectively, which were added together with higher modes to obtain the curve in FIG. 2.
Figure 4:
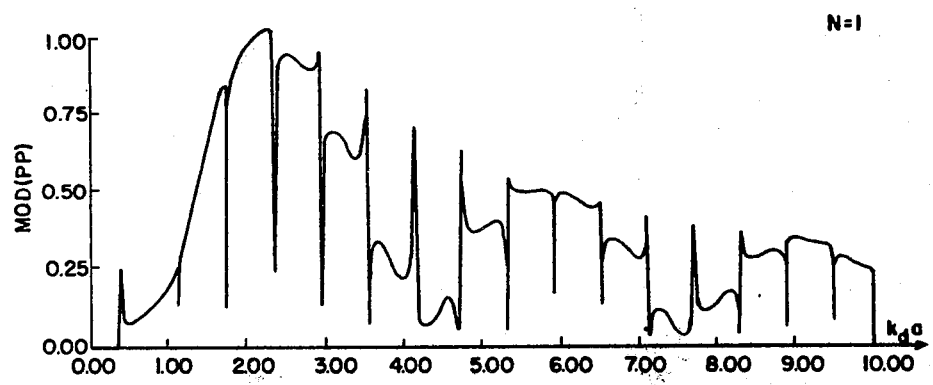

FIGS. 3 and 4 show the amplitude moduli $[f_n^{pp}(\pi)/a]$ of the first two (n=0,1) of the modes which were added together to obtain the curve in FIG. 2.

Figure 5:
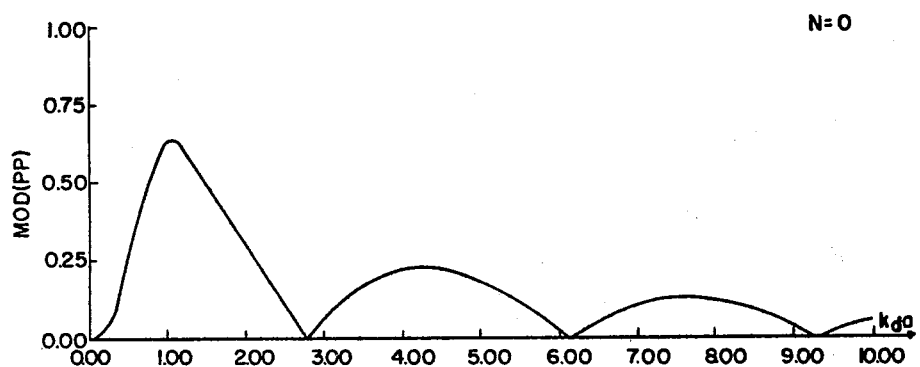
FIGS. 5-6, also for alcohol in aluminum, are graphs of the first two modes (n=0,1) respectively, displaying the moduli of the smooth "background" contributions of an evacuated cavity.
Figure 6:
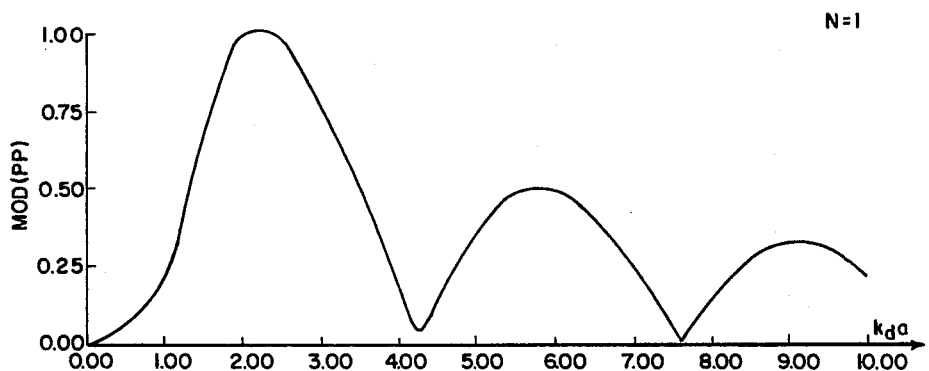

FIGS. 5 and 6, also for alcohol in aluminum, are graphs of the first two modes (n=0,1) respectively of the moduli of the smooth "background" contributions (analogous to the "potential scattering" of quantum theory) of an evacuated cavity, which are obtained by repeating the preceding calculations setting $\rho_f = 0$.

Figure 7:
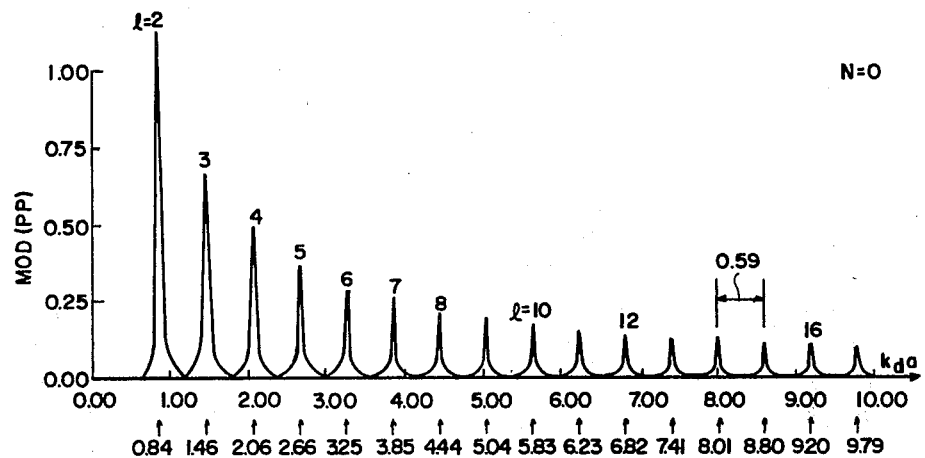
FIGS. 7-8 are graphs displaying the resonances of the modulus for the first two modes (n=0,1) respectively of an alcohol-filled spherical cavity in aluminum.
Figure 8:
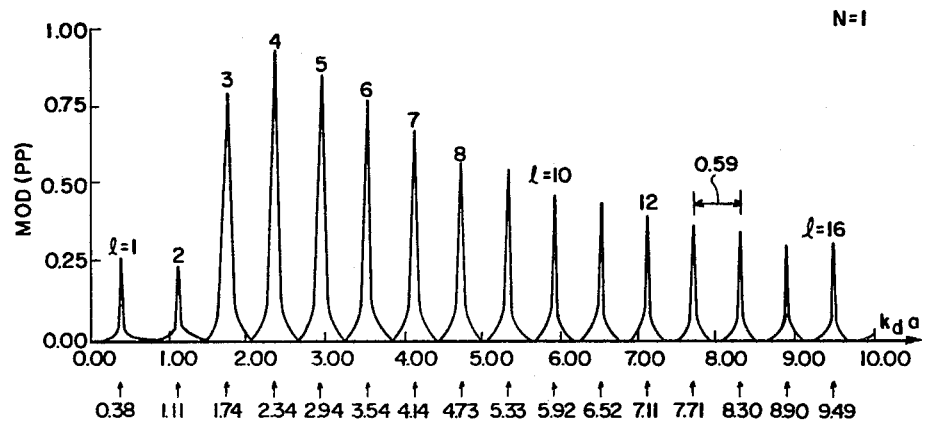

FIGS. 7 and 8, also for alcohol in aluminum and for the first two modes (n=0,1) respectively, show the modulus of the difference of the two aforementioned complex quantities. For each mode n, these resonances are labeled by an index l. The spike labeled l=1 in each mode n, is the fundamental and the others (l=2,3, ...) are the overtones. Each partial wave plot can be physically interpreted as the interference between the smooth "potential scattering" background of an empty cavity, and the resonances of the filler.

Overlaying each set (l=1,2, ...) of resonances for each mode (n=0, 1,2 ...) on top of the summed amplitude of FIG. 2 permits identification of each rapid oscillation or extremum in that plot, with the sets of modal resonances contained in each partial wave contribution. The resonances responsible for each oscillation of FIG. 2 are labeled by indices (n, l), and over thirty oscillations are uniquely identified with resonances in this fashion. Since each substance has its own set of identifying resonances, a "library of signatures" could be constructed and the echo of each new, unknown filler could then be compared to these library entries for identification purposes.

While the "library of signatures" approach is fully effective as a means of identification, there is a second quicker and more direct method available which is dependent on the spacing between high-order overtones and their widths. For example, utilizing plots analogous to FIGS. 3–8 but for water rather then alcohol, contained in the same aluminum matrix, it is found that the set of modal resonances is different from those in FIGS. 3–8; hence, an immediate distinction between the two fillers is quite evident. The location of all the resonance spikes in fact identifies the ratio $c_f/c_d$ of the filler-to-matrix wavespeeds. The filler's sound-speed $c_f$ can be found from the spacing $\Delta$ between any two high-order consecutive overtones shown in FIGS. 3–8. For spherical cavities in solids, the asymptotic spacing $\Delta$ (to be read from FIGS. 3–8) becomes uniform for $l \gg 1$ and it is $\Delta \approx \pi(c_f/c_d)$. For alcohol in aluminum, that relation gives $\Delta \approx 0.59$, just as it is observed in FIGS. 3–8. Thus, knowing $c_d$ for the matrix and the spacing $\Delta$ between consecutive, high-order, modal resonances, determines the sound speed $c_f$ of the filler. Incidentally, the same formula for the asymptotic spacing is also found to hold for cylindrical cavities. A dependence on different cavity shapes is presumably contained in the backgrounds and in the non-uniform spacing of the lower-order resonances. It only remains to determine the density ratio of filler-to-matrix materials, i.e., $\rho_f/\rho$. This is found from the resonance widths.

The expression for the widths is $$F_n \frac{c_d}{c_f} x = \operatorname{Re} z_1(x) - \frac{\operatorname{Im} z_1(x)}{\Gamma_{nl}/2}(x - x_{nl}) \quad (2)$$

where the functions $F_n(x)$ and $z_1(x)$ can be found from the equations $$F_n = (\rho/\rho_f) k_f a [j_n'(k_f a)/j_n(k_f a)]$$

and $$Z_1 = -k_s^2 a^2 \begin{vmatrix} d_{11} & d_{12} \\ d_{31} & d_{32} \end{vmatrix} / \begin{vmatrix} d_{21} & d_{22} \\ d_{31} & d_{32} \end{vmatrix} \equiv A_n^{(s)} + i s_n^{(s)}$$

$$Z_2 = -k_s^2 a^2 \begin{vmatrix} f_1 & d_{12} \\ f_3 & d_{32} \end{vmatrix} / \begin{vmatrix} f_3 & d_{22} \\ f_3 & d_{32} \end{vmatrix} \equiv A_n^{(s)} + i \sigma_n^{(s)}$$

$$\overline{Z}_2 = -k_s^2 a^2 \begin{vmatrix} d_{11} & A_1^* \\ d_{31} & A_3^* \end{vmatrix} / \begin{vmatrix} d_{21} & A_2'^* \\ d_{31} & A_3^* \end{vmatrix} \equiv \overline{A}_n^{(s)} + i \overline{\sigma}_n^{(s)}$$

$$\overline{Z}_1 = Z_1,$$

and the resonance frequencies $x_{nl}$ are the roots of the characteristic equation $\operatorname{Re} z_1 = F_n$. Eq. (2) can be solved for the density ratio $\rho_f/\rho$ contained in the expression for $F_n$. The result can be evaluated at a point one half-width below any resonance peak (i.e., at $x = x_{nl} - \frac{1}{2}\Gamma_{nl} \equiv X_n$) and then expanded asymptotically for $x \gg 1$. In this limit the density ratio admits considerable simplification and it is eventually found that $$\frac{\rho_f}{\rho} \xrightarrow{x \gg 1} \left[ -\frac{1}{x} + \frac{c_d}{c_f} \cot\left(\frac{c_d}{c_f} x - n\frac{\pi}{2}\right) \right]_{x=X_{nl}} \approx \quad (3)$$

$$\left[ -\frac{\pi^2}{\Delta^2} x + \left\{ \frac{\pi^2}{\Delta^2}(l + \frac{n}{2} - \frac{1}{2})\Delta - \frac{1}{(l + \frac{n}{2} - \frac{1}{2})}\Delta \right\} \right]_{x=X_{nl}}$$

where the last expression holds for any integer mode order n, and for $\Gamma_n/2 < \Delta$, the latter condition meaning the resonance half width should be smaller than the asymptotic spacing, so that consecutive resonances do not overlap. It should be noted that in the $x \gg 1$ limit, the zeroes of the first expression given in Eq. (3) are the zeroes of the cotangent function which tend to occur at integer or half-integer multiples of (i.e., $$x_{nl} \xrightarrow{x \gg 1} (l + \frac{n}{2} - \frac{1}{2})\Delta$$

where l is the integer index labeling the pertinent high order overtone of any mode n). Performing the indicated evaluation in Eq. (3) it is found that $$\frac{\rho_f}{\rho} \xrightarrow{x \gg 1} \quad (4)$$

$$-\frac{1}{(l + \frac{n}{2} - \frac{1}{2})\Delta} + \frac{\pi^2}{\Delta^2} \frac{\Gamma_{nl}}{2} \ldots (n, l = \text{integers},)$$

which in the high frequency (i.e., $x \gg 1$) limit, gives the filler-to-matrix density ratio in terms of the uniform asymptotic spacing $\Delta$, and the width $\Gamma_{nl}$ of any (high-index) overtone l, of any mode n. These are all either known or previously determined quantities. The graphs of the (two) functions in the square brackets of Eq. (3) plotted versus x, are steep in the vicinity of the resonances $$x_{nl} \approx (l + \frac{n}{2} - \frac{1}{2})\Delta,$$

at which points they go through zeroes. Therefore the points one half-width below these resonances, where those expressions are evaluated, must be accurately determined in order to obtain good estimates of the density ratio as given in Eq. (4).

For ethyl alcohol ($\rho_f = 0.79$ g/cm$^3$, $c_f = 1.213 \times 10^5$ cm/sec) in aluminum ($\rho = 2.7$ g/cm$^3$, $c_d = 6.420 \times 10^5$ cm/sec), it is found that $\Delta \approx 0.593$, $\pi^2/\Delta^2 = 28.01$ and for the first ($n=1$) mode, the width of its tenth overtone ($l=1.0$), which occurs at $x_{nl} \approx 1\Delta = 5.93$, is $\Gamma_{nl} \approx 0.06$. This width is $\sqrt{3}$ too large since it is read from a plot of $[f_n^{pp}]$ rather than from a plot of $[f_n^{pp}]^2$ which is where the widths are commonly defined. Substituting these values into Eq. (4) yield $\rho_f/\rho \approx 0.296$ which contains about 1% error when compared to the actual ratio 0.79/2.70. Thus, knowing $\rho$ for the matrix, the very simple relation in Eq. (4) gives the filler density $\rho_f$. The filler fluid is completely identified once its sound speed and density are determined by this asymptotic procedure.

Effectively, the process of identification has been completed once the analysis described above has been completed. However, the process described may just as well by pass the use of the chart recorder 25 or CRT 27, and instead convert the signal received from amplifier 23 into a digital output through the use of the analog-to-digital converter 29. It is well within the ability of one with ordinary skill in the computer field to reduce the process above described to a digital program. Accordingly, the output of the analog-to-digital converter 29 could be supplied to the digital computer 31 for analysis, and the resulting material identification would be provided as the output of printer 33.

In summary, the instant apparatus and process permit the complete identification of the material composition of a fluid obstacle of any shape contained within a solid host material. By the subtraction of a suitable non-resonant background from the composite contribution of each partial wave to the echo from a fluid filled cavity in a solid, the resonances of each normal mode can be determined and a clear physical meaning can be given to the individual partial waves as interferences between backgrounds and resonances. The family of spectral resonances found can be used to specifically determine which resonance spike in which particular normal mode causes each rapid oscillation in the cavity's summed amplitude $[f^{pp}]$. In making bistatic (i.e., away from the monostatic $\theta$=direction) determinations of $[f^{pp}(\theta)/a]$ from Eq. (1) at angles $\theta_{nm}$ chosen to be the zeroes of $P_n$ (cos $\theta$) for a given n, the contribution from that $n^{th}$ mode to the summed amplitude in Eq. (1) can be determined. In this manner bistatic measurements or calculations can be used to suppress and further disent angle the selected individual (partial wave) contribution of any given mode n, from the sum of all the others.

The use of this process to decipher the scattering code about material composition contained in the cavity's "echo" has applications to a variety of problems in geophysics, non-destructive material testing and evaluation, oil exploration, and also to scattering from bubbles in liquids, or from certain fluid-like substances (viz. tumors) in animal tissue.

This process can be extended to account for solid inclusions in material media, whereby the material composition of a solid target (of any shape) immersed in a fluid medium can be determined. This is the classical target discrimination identification problem of underwater acoustics of obvious naval importance. For example, using the above method, a sonar operator would be able to tell whether he has contacted a whale or a submarine.

It should be understood, of course, that the foregoing disclosure relates to only a preferred embodiment of the invention and that numerous modifications or alternations may be made therein without departing from the spirit and the scope of the invention as set forth in the appended claims.

What is claimed and desired to be secured by Letters Patent of the United States is:

1. A method for determining the properties of a fluid encapsulated in a cavity within a viscoelastic material comprising the steps of:
    directing an incident wave formed of a series of acoustic pulses having a known frequency spectrum at said viscoelastic material, thereby creating compressional waves in said material that impinge upon said fluid-filled cavity and create therein a set of modal resonances;
    receiving a portion of said waves backscattered from said cavity;
    converting said received waves into electrical signals;
    converting said electrical signals into an echo pattern of said backscattered waves comprising a composite modulus of resonance amplitudes as a function of frequency;
    subdividing said echo pattern into its component partial-wave resonance responses, each of which corresponds to a particular resonance mode;
    determining the background components of said partial-wave responses, said background components being proportional to the resonance response of a cavity having zero density;
    subtracting said background component from a partial-wave response of the same mode, thereby obtaining a spectral response comprising a plurality of resonance peaks corresponding to the fundamental and overtone modal resonances of said partial-wave responses;
    measuring the asymptotic spacing between any two consecutive, high-order modal resonance overtones and obtaining therefrom, for a viscoelastic material having a known wavespeed, the wavespeed of said unknown fluid, said spacing being proportional to the ratio of said unknown fluid wavespeed to said known viscoelastic material wavespeed; and
    determining the width of any of said high-order modal resonance overtones at a point one half-width below the maximum value of said overtone and obtaining therefrom, for a viscoelastic material having a known density, the density of said unknown fluid wherein the ratio of said unknown fluid density to said known viscoelastic material density is proportional to said width, said asymptotic spacing, said partial-wave mode, and said particular high-order modal resonance overtone whose width is being determined, whereby the properties of said unknown fluid in said cavity are defined by said fluid density and the wavespeed within said fluid.

2. The method of claim 1 wherein a viscoelastic material is encapsulated within a fluid medium.

3. The method of claim 1 wherein said step of converting said electrical signals includes the step of:
    plotting said modulus of modal resonance overtones as a function of non-dimensional frequency X, where X is proportional to the angular frequency of said incident waves times the radius of said cavity divided by the speed of said compressional waves in said viscoelastic material.

4. The method of claim 2 wherein said step of converting said electrical signals includes the step of:
    plotting said modulus of modal resonance overtones as a function of non-dimensional frequency X, where X is proportional to the angular frequency of said incident waves times the radius of said cavity divided by the speed of said compressional waves in said viscoelastic material.

5. The method of claims 3 or 4 wherein the high frequency limit of said ratio of said unknown fluid density to said known viscoelastic material density is expressed by the relation:

$$-\frac{1}{\left(l+\frac{n}{2}-\frac{1}{2}\right)\Delta}+\frac{\pi^2\Gamma nl}{2\Delta^2}$$

where n is an integer equal to the particular partial-wave mode being analyzed, l is an integer equal to a high-order modal overtone resonance, $\Gamma$ is the width of overtone l, and $\Delta$ is the asymptotic spacing between overtone l and overtone (l+1).

6. A method for determining the properties of a fluid encapsulated in a cavity within a viscoelastic material comprising the steps of:
    directing an incident wave formed of a series of acoustic pulses having a known frequency spectrum at said viscoelastic material, thereby creating compressional waves in said material that impinge upon said fluid-filled cavity and create therein a set of modal resonances;
    receiving a portion of said waves backscattered from said cavity;
    converting said received waves into electrical signals;
    converting said electrical signals into an echo pattern of said backscattered waves comprising a composite modulus of resonance amplitudes as a function of frequency;

subdividing said echo pattern into its component partial-wave resonance responses, each of which corresponds to a particular resonance mode;

determining the background components of said partial-wave responses, said background components being proportional to the resonance response of a cavity having zero density;

subtracting said background component from a partial-wave response to the same mode, thereby obtaining a spectral response comprising a plurality of resonance peaks corresponding to the fundamental and overtone modal resonances of said partial-wave responses;

compiling a plurality of said partial-wave spectral responses for each of a plurality of known fluids in known viscoelastic materials; and comparing said known partial-wave spectral responses to the spectral response of an unknown fluid-filled cavity in a known viscoelastic material, said unknown fluid being identified when a correlation occurs between a set of known responses and said unknown fluid responses.

7. The method of claim 6 wherein a viscoelastic material is encapsulated within a fluid medium.

* * * * *